(12) United States Patent
Banerjee et al.

(10) Patent No.: US 7,534,611 B2
(45) Date of Patent: May 19, 2009

(54) SULFUR-OXIDIZING PLANT GROWTH PROMOTING RHIZOBACTERIA FOR ENHANCED CANOLA PERFORMANCE

(76) Inventors: Manas Ranjan Banerjee, P.O. Box 99 St. Norbert Postal Station, Winnipeg, MB (CA) R3V 1L5; Laila Yesmin, P.O. Box 99 St. Norbert Postal Station, Winnipeg, MB (CA) R3V 1L5

( * ) Notice: Subject to any disclaimer, the term of this patent is extended or adjusted under 35 U.S.C. 154(b) by 39 days.

(21) Appl. No.: 11/844,386

(22) Filed: Aug. 24, 2007

(65) Prior Publication Data

US 2008/0242543 A1 Oct. 2, 2008

Related U.S. Application Data

(62) Division of application No. 10/319,645, filed on Dec. 16, 2002, now Pat. No. 7,491,535.

(60) Provisional application No. 60/344,817, filed on Jan. 7, 2002.

(51) Int. Cl.
  *C12N 5/00* (2006.01)
  *C12N 5/02* (2006.01)
(52) U.S. Cl. ..................... 435/410; 435/420
(58) Field of Classification Search ............. None
  See application file for complete search history.

(56) References Cited

U.S. PATENT DOCUMENTS 6,277,814 B1 * 8/2001 Qiu et al. .................. 514/2

* cited by examiner

*Primary Examiner*—Mark Navarro
(74) *Attorney, Agent, or Firm*—Michael R. Williams; Ade & Company Inc.

(57) ABSTRACT

Described herein is the isolation and identification of a number of sulfur oxidizing plant growth promoting rhizobacteria: RAY12, identified as *Achromobacter piechaudii*; RAY28, identified as *Agrobacterium tumefaciens*, RAY132, identified as *Stenotrophomonas maltophilia*; and RAY209, identified as *Delftia acidovorans*. The PGPR act to oxidize elemental sulfur which in turn provides sulfate for the plants. As a result of this arrangement, plants are able to grow more efficiently and effectively and have enhanced growth characteristics, for example, but by no means limited to, increased vigor, early emergence, increased emergence rate, increased biomass, increased plant leaf area, higher crop yield, increased pod number, increased pod weight, increased root biomass, increased seed weight, increased macro- and micro-nutrient uptake and the like. The sulfur-oxidizing PGPR may be applied to seeds, seed pieces, carrier materials, roots and planting soil.

12 Claims, 7 Drawing Sheets

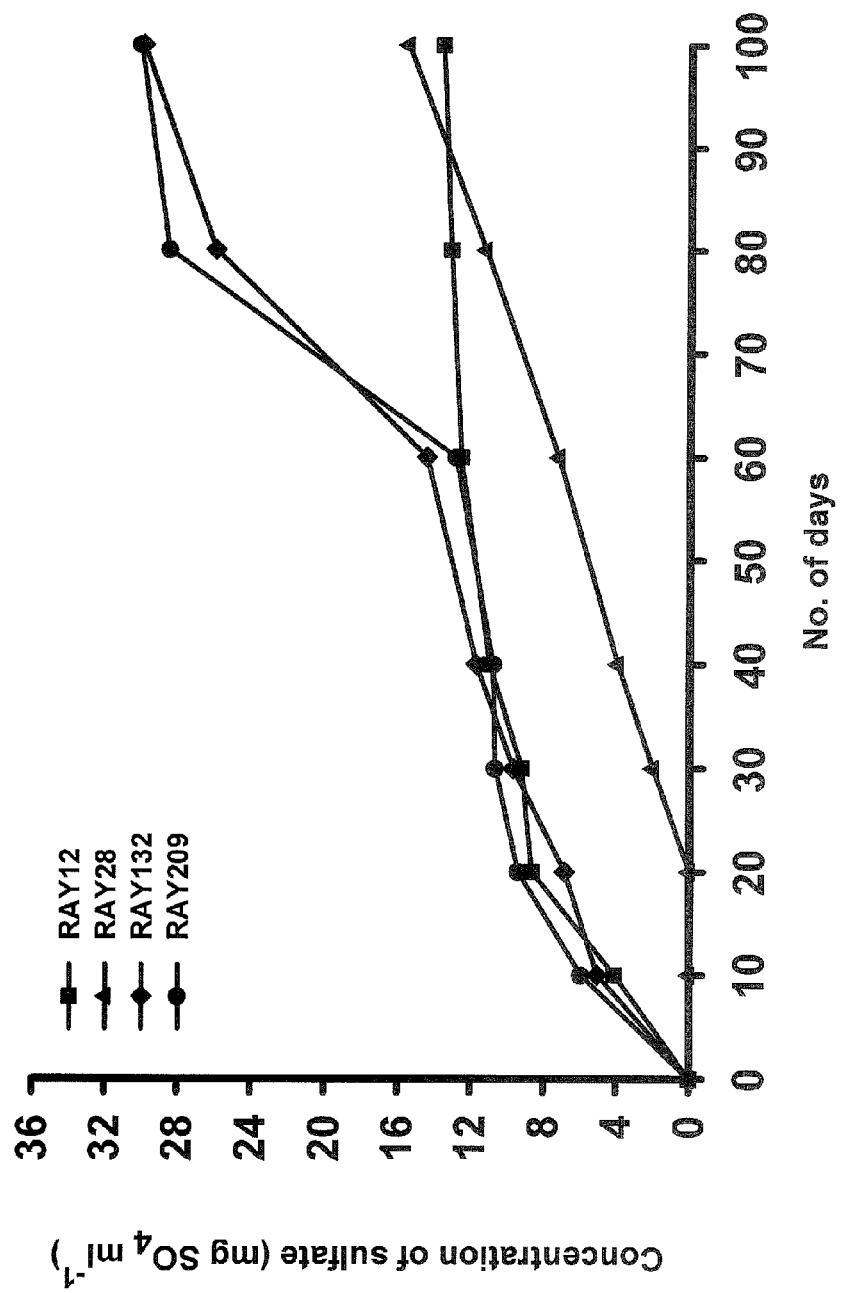
Figure 1. Sulfate production by rhizobacterial strains

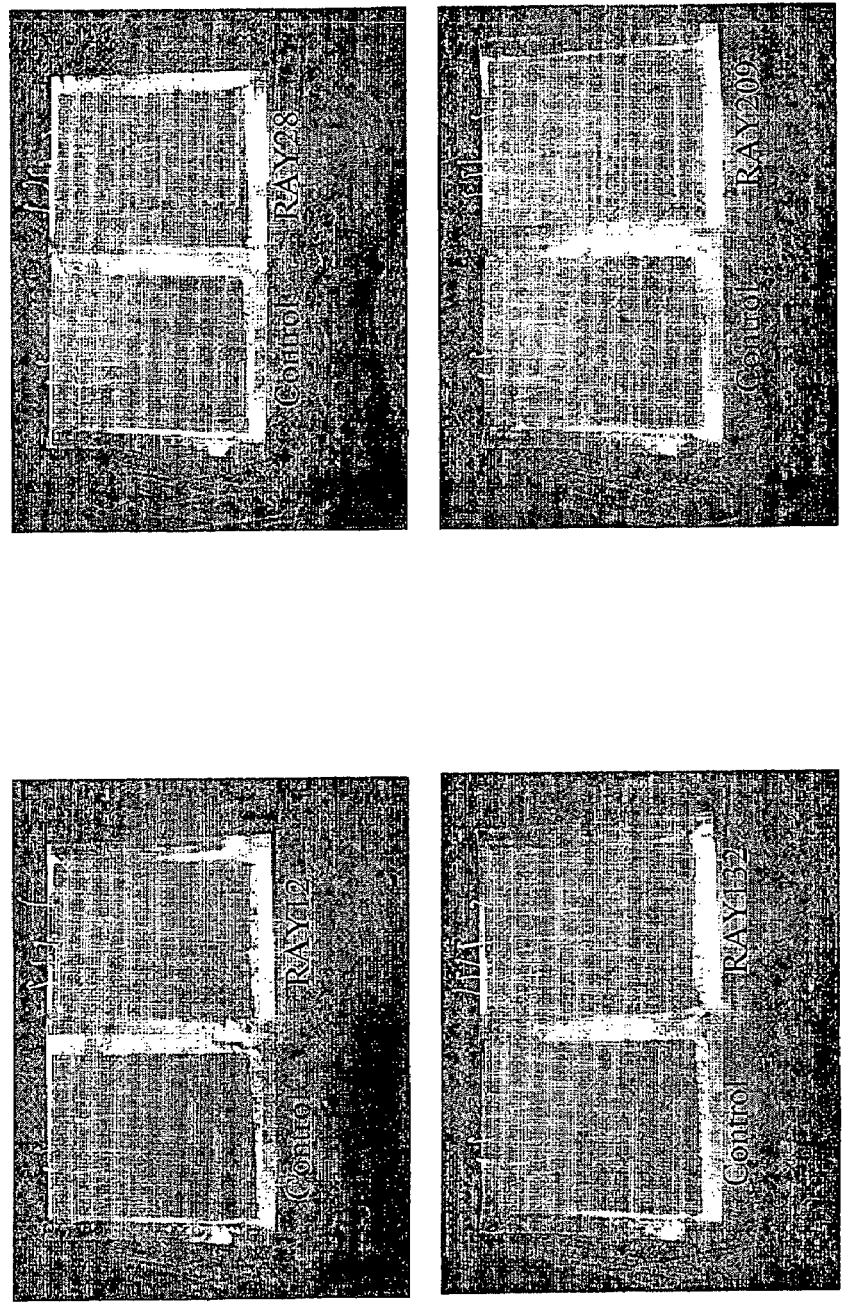
Figure 2. Canola seeds inoculated with PGPR strains grown in growth pouch at 4 days

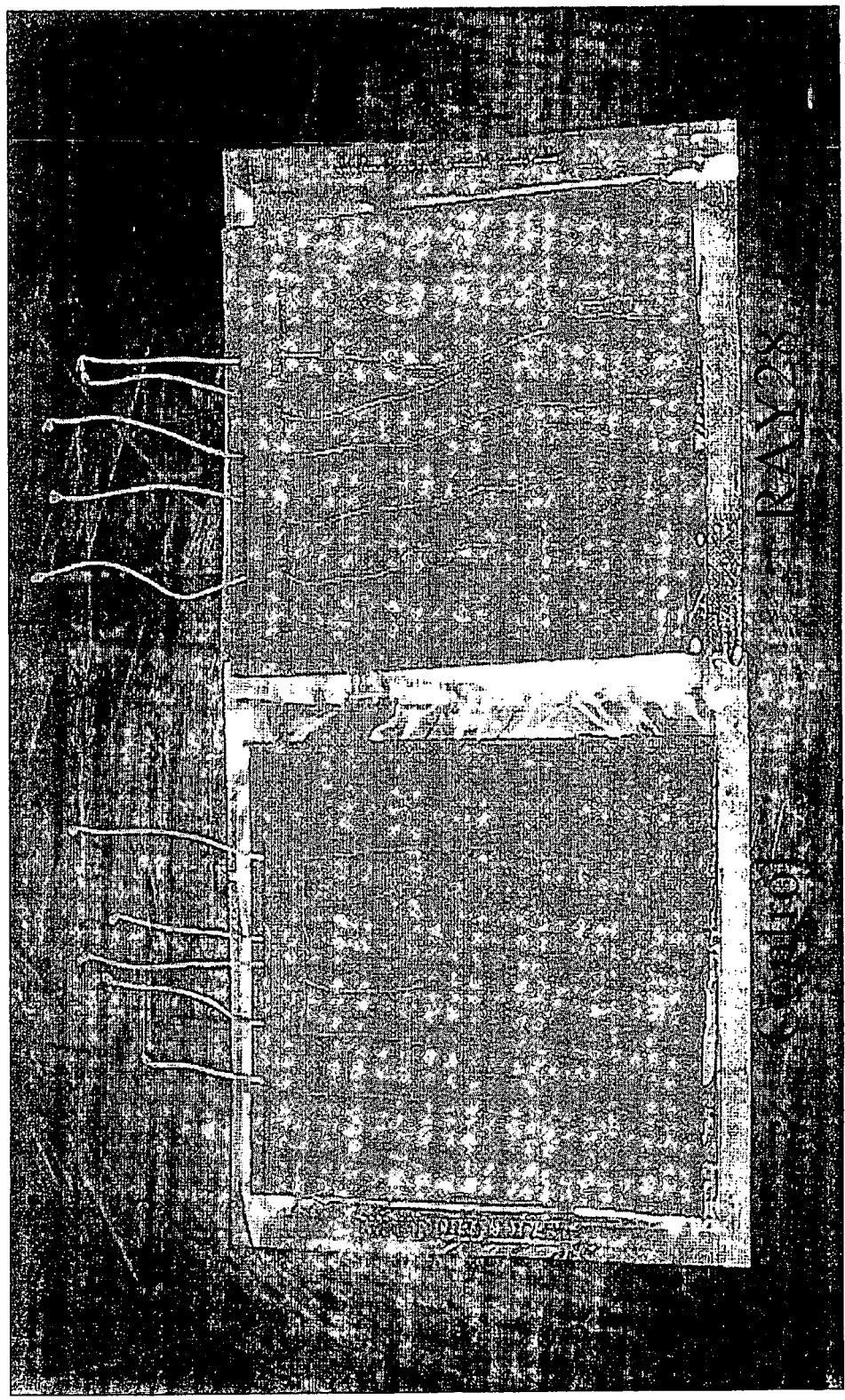
Figure 3. Canola seeds inoculated with PGPR strains grown in growth pouch at 7 days

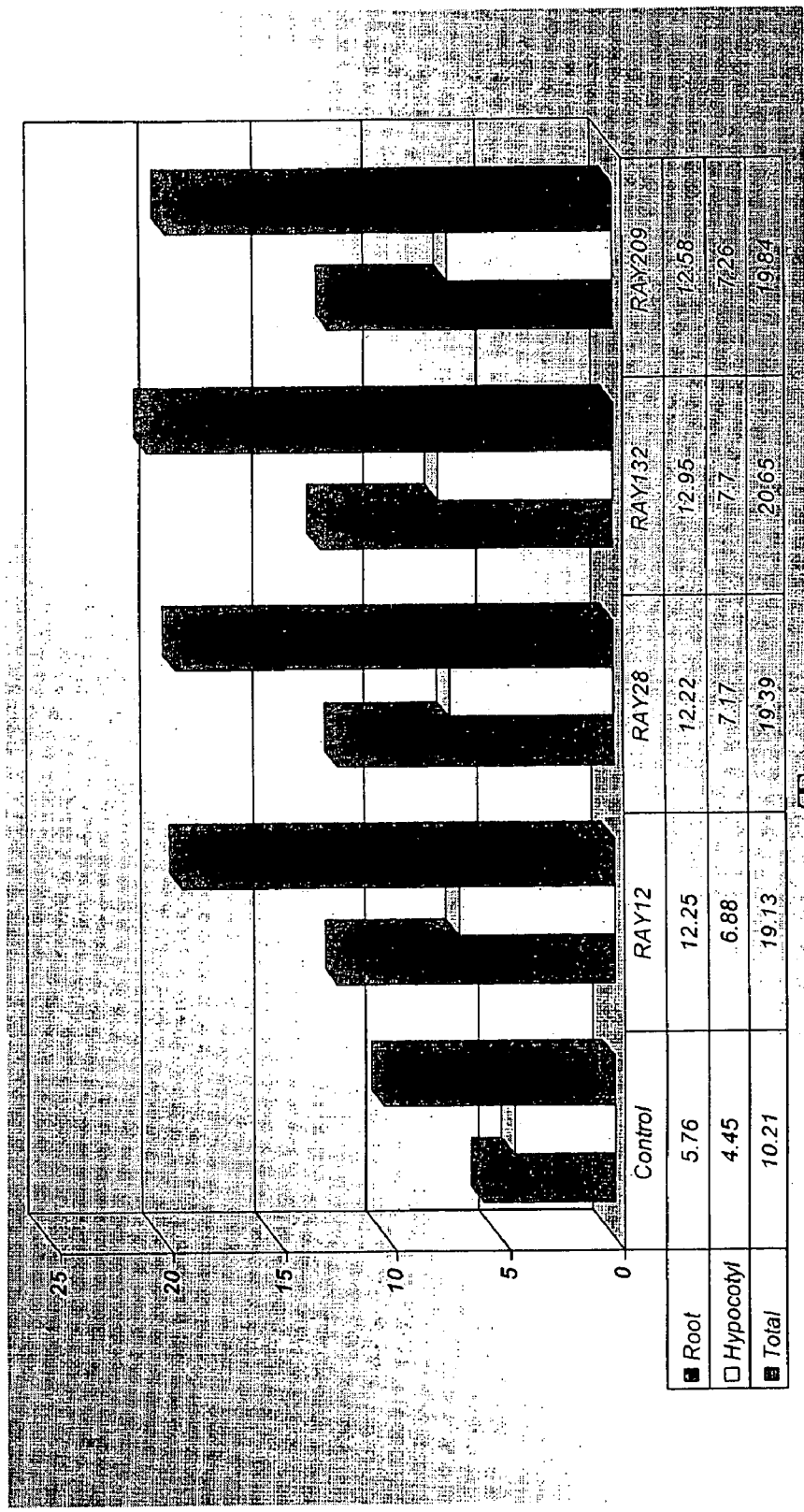
Figure 4. Effect of seed inoculation on root and hypocotyl length in 7 days

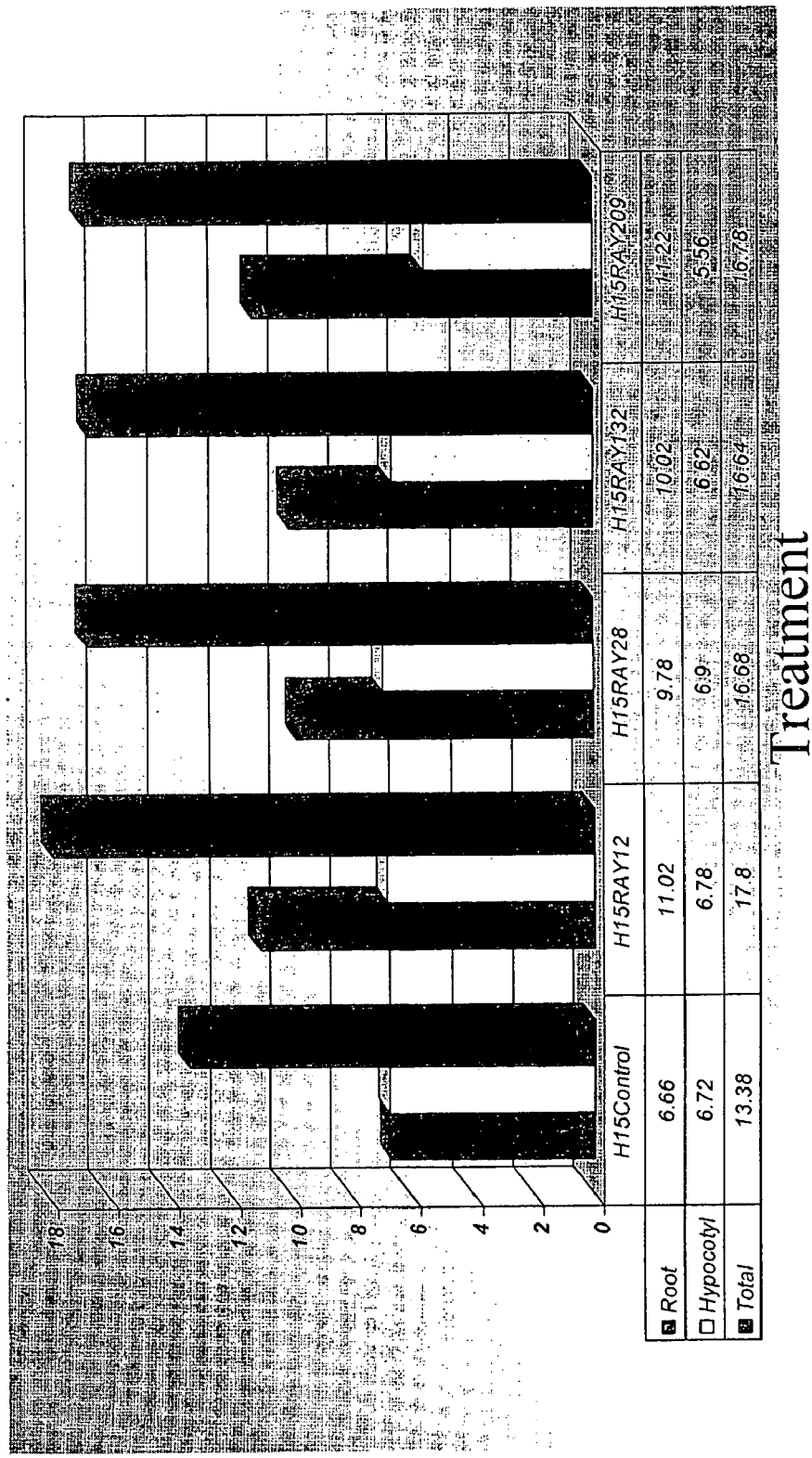
Figure 5. Effect of inoculation of Helix treated seed on root and hypocotyl length in 7 days

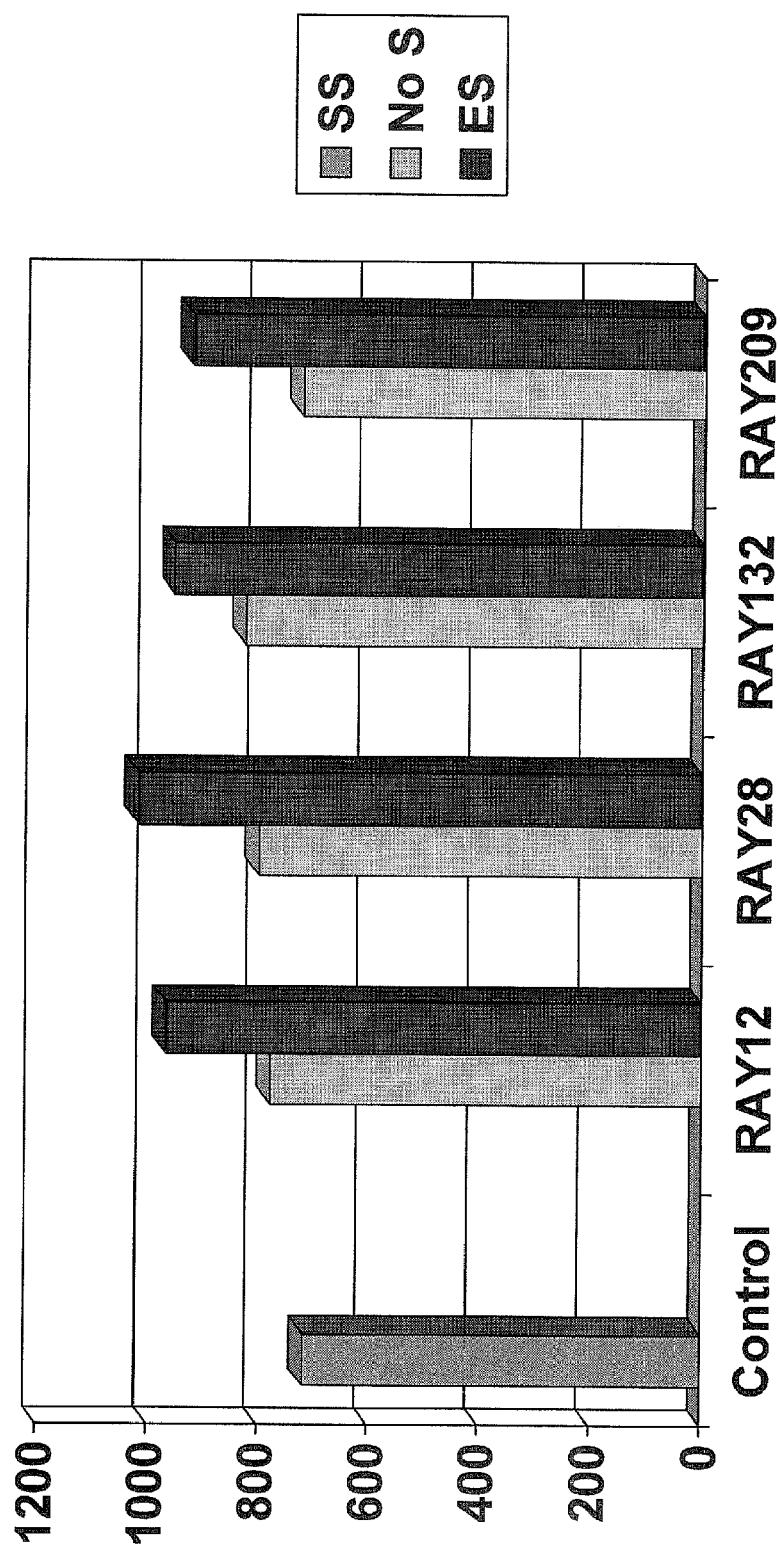
Figure 6. Canola yield (kg/ha) in 2001 field trial in Miami, MB

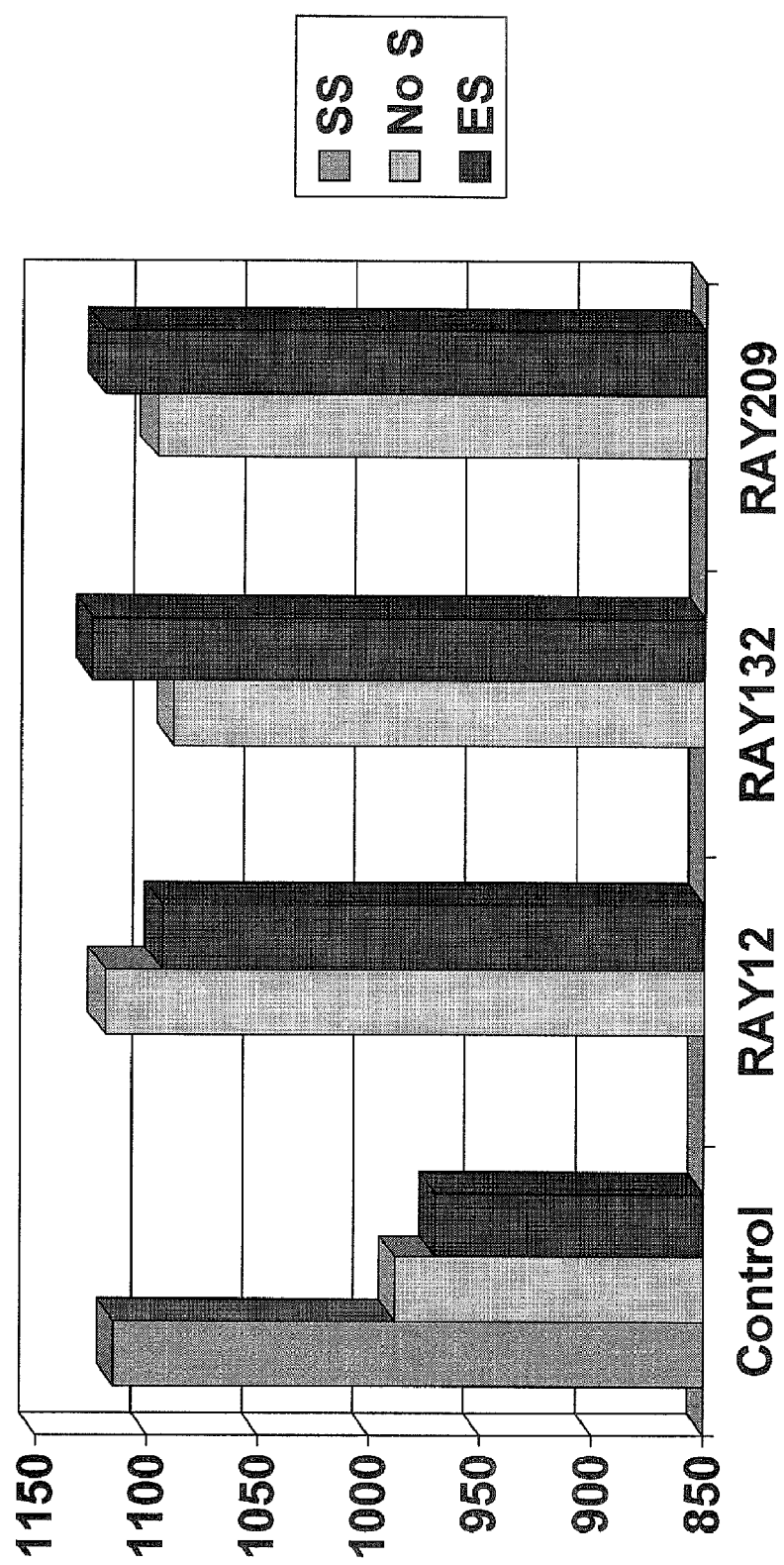
Figure 7. Canola yield (kg/ha) in 2002 field trial in Dauphin, MB

SULFUR-OXIDIZING PLANT GROWTH PROMOTING RHIZOBACTERIA FOR ENHANCED CANOLA PERFORMANCE

PRIOR APPLICATION

This application is a divisional application of U.S. patent application Ser. No. 10/319,645, filed Dec. 16, 2002, now U.S. Pat. No. 7,491,535, which claims priority under 35 USC § 119(e) to Provisional Patent Application Ser. No. 60/344,817 filed on Jan. 7, 2002.

FIELD OF THE INVENTION

The present invention relates generally to the field of seed treatments. More specifically, the present invention relates to biological seed treatment by naturally occurring sulfur-oxidizing rhizobacteria to enhance canola performance in an environmentally friendly manner.

BACKGROUND OF THE INVENTION

Recent advances in soil microbiology and biotechnology have resulted in renewed interest to the use of microbial inoculants in agriculture, forestry and environmental management. Among the microbial inoculants, bacteria from the plant's rhizosphere and rhizoplane (rhizobacteria), are receiving considerable attention with respect to plant growth promotion. Rhizobacteria influence plant growth via different mechanisms, however, beneficial interactions are often difficult to identify and isolate for study, therefore favorable effects on plant productivity are not easily demonstrated in quantitative terms (Gaskin et al., 1985, *Agriculture, Ecosystems and Environment* 12: 99-116). The rhizobacteria which colonize plant roots and stimulate plant growth are known as plant growth promoting rhizobacteria (PGPR, Kloepper et al., 1988, *Plant Dis* 72: 42-46). Positive effects of PGPR were initially limited to root crops, like radish (Kloepper and Schroth, 1978, in *Proceedings of the Fourth International Conference on Plant Pathogenic Bacteria*, vol. 2: 879-882), potato (Burr et al., 1978, *Phytopathology* 68: 1377-1383) and sugarbeet (Suslow and Schroth, 1982, *Phytopathology* 72: 199-206). Later reports suggested PGPR have positive influence on diversified crops, such as bean (Anderson and Guerra, 1985, *Phytopathology* 75: 992-995), barley (Iswandi et al., 1987, *Biol Fed Soils* 3; 153-158), vegetables (Elad et al., 1987, *Plant Soil* 98: 325-330), canola (Kloepper et al., 1988; Grayston and Germida, 1991, *Canadian Journal of Microbiology* 37: 521-529; Banerjee, 1995 in *Phytochemicals and Health*, (Gustine and Flores, eds) pp 179-181), cotton (Backman and Turner, 1989, in *Proceedings Beltwide Cotton Products Research Conference, Book 2* (Brown, ed) pp 16-17), pea (Chanway et al., 1989, *Soil Biology and Biochemistry* 21: 511-517), peanut (Turner and Backman, 1991, *Plant Disease* 75: 347-353) and many other crops. Several mechanisms have been postulated so far to explain the PGPR's positive impact on plant growth enhancement. Probably the most successful and well-known microbial inoculant for agricultural crops is that based on *Rhizobium* spp. through symbiotic nitrogen fixation. Kapulinik et al., (1981, *Experimental Agriculture* 17: 179-188) showed nitrogen fixation as a mechanism for yield increases in summer cereal crops of Israel in fields inoculated with *Azospirillum*. Several rhizobacteria like *Azotobacter* spp. are capable of producing a vast array of phytohormones (e.g. auxins, cytokinins) and enzymes (e.g. pectinase) which are intimately involved in the infection process of symbiotic bacteria-plant associations which have a regulatory influence on nodulation by *Rhizobium* (Okon and Hadar, 1987, *CRC Critical Reviews in Biotechnology* 6: 61-85). Some PGPR strains that induced yield increases of potato were reported (Kloepper et al., 1980a, *Nature* 286: 885-886) to produce extracellular siderophores that bind $Fe^{3+}$, making it less available to certain member of natural microflora. These rhizobacteria excrete low molecular weight, high affinity ferric-chelating microbial cofactors which specifically enhance their acquisition of iron by binding to membrane bound siderophore receptors. One of the siderophores produced by some pseudomonad PGPR is known as pseudobactin that inhibits the growth of *Erwinia cartovora* (causal organism for soft-rot of potato) (Kloepper et al., 1980b, *Current Microbiology* 4: 317-320). Additions of pseudobactin to the growth medium inhibited soft-rot infection and also reduced the number of pathogenic fungi in the potato plant along with a significant increase in potato yield. Most evidence to support the siderophore theory of biological control by PGPR comes from work with the pyoverdines, one class of sideophores that comprises the fluorescent pigments of fluorescent pseudomonads (Demange et al., 1987 in Iron Transport in Microbes, Plants and Animals (Winkleman et al, eds.), pp 167-187). According to the siderophore theory, pyoverdines demonstrate functional strain specificity is due to selective recognition of outer membrane siderophore receptors (Bakker et al., 1989, *Soil Biology and Biochemistry* 19: 443-450). Many PGPR produce a wide variety of phytohormones (e.g. auxins, gibberellins, cytokinins) in the rhizosphere. For example, pseudomonads are reported to produce indole acetic acid (IAA) and to enhance the amounts of IAA in plants that have a profound impact of plant biomass production (Brown, 1974, *Annual Review of Phytopathology* 12: 181-197). Tien et al. (1979, *Applied Environmental Microbiology* 37: 1016-1024) found that inoculation of nutrient solutions around roots of pearl millet with *Azospirillum brasilense* resulted in increased shoot and root weight, an increased number of lateral roots, and all lateral roots were densely covered with root hairs. They reported that supplying the plants with combinations of IAA, gibberllins and kinetin caused increased production of lateral roots similar to that caused by azospirilla. Although the biological significance of these phytohormones and plant-hormone-like materials are not totally understood, the growth stimulating activity of these microorganisms are commonly attributed to their production of these materials. The PGPR also affect the plant growth and development by modifying nutrient uptake. The extent to which they promote uptake of mineral nutrients is a topic of considerable debate. They may alter nutrient uptake rates by direct effects on roots, by effects on the environment which in turn modify root behavior, and by competing directly for nutrients (Gaskin et al, 1985). Some factors in which PGPR may play a role in modifying the nutrient use efficiency in soils are root geometry, nutrient solubility, nutrient availability by producing plant congenial ion form, partitioning of the nutrients in plant and utilization efficiency. For example, increased solubilization of inorganic phosphorous in soil (Brown, 1974, *Annual Review of Phytopathology* 68; 181-197), enhanced $^{32}P$ uptake in canola seedling using *Pseudomonas putida* (Lifshitz et al., 1987, *Canadian Journal of Microbiology*), and, increased sulfur-oxidation and sulfur uptake (Grayston and Germida, 1991; Banerjdee, 1995). Nevertheless, factors affecting the success of a microbial inoculation or PGPR inoculation in soil include considerations at all stages of inoculum use—strain selection, culturing of the strain, carrier preparation, mixing of the culture and carrier, maturation, storage, transport and application (Killham, 1994, in Soil Ecology, pp 182-211).

U.S. Pat. No. 5,589,381 teaches the isolation of a biocontrol element comprising a *Bacillus licheniformis* strain which controls *Fusarium* seedling blight in corn.

U.S. Pat. No. 5,503,652 teaches the isolation of strains capable of promoting root elongation in plants.

U.S. Pat. No. 5,935,839 teaches the use of *Arthrobacter* sp. and *Pseudomonas fluorescens* for promoting growth of conifer seedlings wherein the PGPR are selected based on their ability to grow in cold and acidic soils typical of conifers.

U.S. Pat. No. 5,503,651 teaches the use of PGPR strains in promoting growth of cereals, oil seed crops and maize based on the chemotactic and root-colonizing capabilities of the strains.

U.S. Pat. No. 5,496,547 teaches the isolation of *Pseudomonas* mutants which are effective biocontrol agents against *Rhizoctonia solani*.

U.S. Pat. No. 4,849,008 teaches applying *Pseudomonas* to the roots, plants, seeds, seed pieces or soil of root crops for enhancing the yield of the root crops.

U.S. Pat. No. 4,584,274 teaches bacteriophage-resistant *Pseudomonas* strains useful in promoting growth of root crops.

U.S. Pat. No. 6,194,193 teaches the use of a formulation for enhancing plant growth which comprises a mixture of *Bacillus* and *Paenbacillus* strains which produce phytohormones.

As the crop deficiencies of sulfur (S) have been reported with greater frequencies over the past several years focused attention has been given on the importance of S as plant nutrient. In many parts in the world S deficiency has been considered as a crucial factor for adequate crop production. Especially in Western Europe incidence of S deficiency has increasingly reported in *Brassica* over the last decade (Scherer, 2001 *European Journal of Agronomy* 14: 81-111). Canola (*Brassica napus* L cv) is one of the most vital oil seed crops in some of the states in US and in the prairie regions of western Canada. However, canola has the highest sulfur (S) demand of any crop grown in these region and as a consequence the yield of canola is seriously affected in soils with low S-supplying capacity. During vegetative growth canola shows very high S demand and symptoms of S deficiency can be seen when grown in most of the S-deficient soils. For example, out of 10 million acres of canola grown areas in the Canadian prairies about 20-25% lands are S-deficient. If canola is grown in those region S-deficiency symptoms will be shown and canola yield will be reduced. In order to meet the crop requirement of S and to alleviate S deficiencies in soils, various types of fertilizers can be used (e.g. sulfate forms and elemental forms of S). Elemental S fertilizer has been recommended because they are the least expensive, there are large reserves of elemental S and they are available as a by-product of the processing of natural gas. Yield response to elemental S, however, is often lower than those of other forms of S fertilizers. This is because elemental S must be oxidized to the sulfate form to be available for plant uptake. The S transformation pathway is as follows: Elemental S $(S^0) \rightarrow$ thiosulfate $(S_2O_3^{2-}) \rightarrow$ tetrathionate $(S_4O_6^{2-}) \rightarrow$ trithionate $(S_3O_6^{2-}) \rightarrow$ sulfite $(SO_3^{2-}) \rightarrow$ sulfate $(SO_4^{2-})$. This oxidation process is largely carried out by S-oxidizers such as bacteria (most active S-oxidizer), e.g. *Thiobacillus* sp.; fungi, e.g. *Fusarium* sp.; and actinomycetes, e.g. *Streptomyces* sp. The forms in bold are mainly stable form and others are unstable. S-oxidizers can utilize elemental S or thiosulfate or both as their substrate for their proliferation. This rate of oxidation, however, largely depends on soil microbial activity. The nature and activity of S oxidizing microorganisms in soils has been a controversial and potential topic. Although the fundamental concept of the enhanced elemental S oxidation by the appropriate soil isolates were proven (Grayston and Germida, 1991; Banerjee, 1995) the success of utilizing the S-oxidizing PGPR in different agro-climatic condition is yet to be determined. Nevertheless, biological seed treatment of canola with naturally occurring S-oxidizing PGPR has tremendous potential to enhance canola performance with lower input cost in the canola growing areas (Banerjee and Yesmin, 2000, Agronomy Abstracts, pp 257, Annual Meeting, Soil Science Society of America). The present invention utilizes S-oxidizing rhizobacteria in canola as microbial seed treatment to enhance soil S-oxidation, crop S-nutrition and as a whole, canola performance. Thus, these rhizobacteria can be used as canola plant growth promoting rhizobacteria (canola PGPR) to enhance the canola growth, development and production.

Although PGPR may reveal huge potential for canola production, for a microbial inoculant to be commercially successful, it must be economically mass-produced and then formulated into a form that is cost-effective, uniform, and readily applicable by the end-user (Walter and Paau, 1997 in Soil Microbial Ecology: Applications in Agricultural and Environmental Management, pp 579-594). Yet, much of the research has gone into identifying and characterizing the potential microbial agent, little has been done on these aspects. According to Glass (1997 in Soil Microbial Ecology Applications in Agricultural and Environmental Management, pp 595-618), several obstacles must be overcome to achieve the successful commercialization of these new generation products. First, microbial products are comprised of living organisms; therefore, they must be produced, formulated and sold in ways such that their viability and biological activity are maintained. Second, microbial products must compete in the marketplace with a huge number of synthetic chemicals, which are more well-known to the end-users (e.g. farmers). Finally, microbial products suffer a bad reputation based on perceived deficiencies with some earlier biological products. Moreover, the success of microbial inoculation for enhanced crop production is greatly influenced by the number of viable cells introduced into soil (Duquenne et al., 1999, *FEMS Mirobiology Ecology* 29: 331-339) as well as biological activity may also decline rapidly with handling and storage procedure if not properly done. Thus, it is crucial to determine the duration of bacterial survivability after the bacterial seed treatment and to obtain the desired level of microbial population for the inoculant to be effective. For example, coating of bacteria treated canola seeds seals bacteria onto the seeds and prevents cells from drying out and keeps bacteria alive much longer than bare seeds. There are now other methods of delivery that are both practical and ecologically sound. But little progress has been made with alternative carriers that might enhance the numerical quality of microbial inoculants (Brockwell and Bottomley, 1995, *Soil Biology and Biochemistry*, 27: 683-697). Daza et al. (2000, *Soil Biology and Biochemistry*, 32: 567-572) evaluated a peat and a perlite-based inoculants and suggested the existence of interactions between carriers and adhesives, and showed that combination of a sucrose adhesive with the perlite carrier gave better survival of bacteria on seeds. Therefore, developing new carrier materials and/or testing of compatibility of different existing commercial inoculant carrier materials for using in the biological seed treatment is urgently needed. Moreover, additional investigation is also needed to compare pure culture strains vs complimentary mixed strains of microorganisms to form synergistic consortia that might have greater potential to give a consistent performance with better competitive ability under different environmental and growth conditions, especially in canola (Yesmin and Banerjee, 2001, in *Proceedings of Saskatchewan Soils and Crops Workshop* 2001, pp 314-319).

In most canola growing areas in the Canadian prairies (Saskatchewan, Manitoba and Alberta) fungicide treated seeds are commonly used as an important element to control plant diseases. These fungicides/insecticides (e.g. Vitavax RS Flowable, Helix, Gaucho) formulated as a suspension is used as seed treatment of canola to control seed decay, pre-emergence damping off, soil-borne blackleg and insect-flea beetles. It is expected that the microbial cultures (e.g. bacteria) might not survive with these pesticides at the recommended doses due to their high toxicity towards living organisms (Yesmin and Banerjee, 2000, *Agronomy Abstracts*, Annual Meeting, pp 257, Soil Science Society of America; Yesmin and Banerjee, 2001). Nevertheless, chance of survivability of these microbial agents may be enhanced if applied with reduced rate. As environmental concerns about groundwater quality and pesticide exposure in foods grow, biological alternatives are becoming necessary (Walter and Paau, 1997). Thus, developing biological treatment compatible to pesticides or even reducing the amount of these carcinogens could be a real boon to the agricultural industry. It is quite likely that the use of inoculants will become a routine technology in the future to increase crop production, cure problems with nutrient uptake and control of plant pathogens. But much works are needed urgently to demonstrate the mass production of inoculants, other than rhizobia, is technologically and economically viable.

SUMMARY OF THE INVENTION

According to a first aspect of the invention, there is provided a bacterial culture selected from the group consisting of: a biologically pure culture of RAY12, identified as *Achromobacter piechaudii*; a biologically pure culture of RAY28, identified as *Agrobacterium tumefaciens*; a biologically pure culture of RAY132, identified as *Stenotrophomonas maltophilia*; a biologically pure culture of RAY209, identified as *Delftia acidovorans*; and mixtures thereof.

According to a second aspect of the invention, there is provided a bacterial culture selected from the group consisting of: a biologically pure culture of RAY12, identified as *Achromobacter piechaudii*; a biologically pure culture of RAY28, identified as *Agrobacterium tumefaciens*; a biologically pure culture of RAY132, identified as *Stenotrophomonas maltophilia*; a biologically pure culture of RAY209, identified as *Delftia acidovorans*; and mixtures thereof are capable of oxidizing elemental S to thiosulfate; capable of oxidizing thiosulfate to sulfate; and capable of oxidizing elemental S to sulfate.

According to a third aspect of the invention, there is provided a method of enhancing plant growth comprising:

inoculating a soil environment with at least one sulfur-oxidizing PGPR, selected from the group consisting of RAY12, identified as *Achromobacter piechaudii*; RAY28, identified as *Agrobacterium tumefaciens*, RAY132, identified as *Stenotrophomonas maltophilia*; and RAY209, identified as *Delftia acidovorans*; and growing a plant in said soil environment.

According to a fourth aspect of the invention, there is provided a composition of matter comprising at least one sulfur-oxidizing PGPR, selected from the group consisting of RAY12, identified as *Achromobacter piechaudii*; RAY28, identified as *Agrobacterium tumefaciens*, RAY132, identified as *Stenotrophomonas maltophilia*; and RAY209 identified as *Delftia acidovorans*; and an agriculturally compatible carrier.

According to a fifth aspect of the invention, there is provided a seed coated with at least one sulfur-oxidizing PGPR, selected from the group consisting of RAY12, identified as *Achromobacter piechaudii*; RAY28, identified as *Agrobacterium tumefaciens*, RAY132, identified as *Stenotrophomonas maltophilia*; and RAY209, identified as *Delftia acidovorans*.

According to a sixth aspect of the invention, there is provided the use of the bacterial strains described above or mixtures thereof as a biocontrol agent.

According to a seventh aspect of the invention, there is provided the use of the bacterial strains described above or mixtures thereof as a biofungicide.

According to a eighth aspect of the invention, there is provided a method of reducing fungicide use in a soil environment comprising:

inoculating a soil environment with at least one sulfur-oxidizing PGPR, selected from the group consisting of RAY12, identified as *Achromobacter piechaudii*; RAY28, identified as *Agrobacterium tumefaciens*, RAY132, identified as *Stenotrophomonas maltophilia*; and RAY209, identified as *Delftia acidovorans*; and growing a plant in said soil environment.

BRIEF DESCRIPTION OF THE DRAWINGS

FIG. 1: Sulfate production capabilities of the PGPR strains RAY12, RAY28, RAY132 and RAY209 by oxidizing elemental sulfur were depicted. Thus, these strains are sulfur oxidizing rhizobacteria.

FIG. 2: Growth of canola roots was depicted after canola seeds inoculated with PGPR strains RAY12, RAY28, RAY132 and RAY209 compared to control in growth pouch at 4 days. All of these strains enhanced the root growth in comparison to control.

FIG. 3: Growth of canola roots was depicted after canola seeds inoculated with PGPR strain RAY28 compared to control in growth pouch at 7 days. The strain RAY28 enhanced the root and hypocotyls growth significantly in comparison to control.

FIG. 4: Growth of canola roots and hypocotyls was measured after canola seeds inoculated with PGPR strains RAY12, RAY28, RAY132 and RAY209 compared to control in growth pouch at 7 days. All of these bacterial strains enhanced the root and hypocotyls growth significantly in comparison to uninoculated control.

FIG. 5: Growth of canola roots and hypocotyls was measured after fungicide (Helix) treated canola seeds inoculated with PGPR strains RAY12, RAY28, RAY132 and RAY209 compared to control in growth pouch at 7 days. All of these bacterial strains enhanced the root and total plant growth significantly in comparison to uninoculated control showing that these bacterial strains were compatible with Helix fungicide.

FIG. 6: Canola yield in Miami, MB field trial site in year 2001. The PGPR+ES treatment on an average increased canola yield by 35% over the sulfate sulfur control. The PGPR treatment alone on an average increased canola yield by 9% over the sulfate sulfur control.

FIG. 7: Canola yield in Dauphin, MB field trial site in year 2002. The PGPR+ES treatment on an average increased canola yield by 14.7% over the elemental sulfur control and 12.7% over the no sulfur control. The PGPR treatment alone on an average increased canola yield by 13.5% over the elemental sulfur control and 11.5% over the no sulfur control.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

DEFINITIONS

As used herein, *Achromobacter piechaudii* RAY12 means a strain of *Achromobacter piechaudii* deposited in accordance with the Budapest Treaty on the International Recognition of the Deposit of Microorganisms for the Purpose of Patent Procedure, on Apr. 16, 2002, at American Type Culture Collection (ATCC), 10801 University Blvd., Manassas, Va. 20110-2209, USA and having the designation PTA-4231.

As used herein, *Agrobacterium tumefaciens* RAY28 means a strain of *Agrobacterium tumefaciens* deposited in accordance with the Budapest Treaty on the International Recognition of the Deposit of Microorganisms for the Purpose of Patent Procedure, on Apr. 16, 2002, at American Type Culture Collection (ATCC), 10801 University Blvd., Manassas, Va. 20110-2209, USA and having the designation PTA-4232.

As used herein, *Stenotrophomonas maltophilia* RAY132 means a strain of *Stenotrophomonas maltophilia* deposited in accordance with the Budapest Treaty on the International Recognition of the Deposit of Microorganisms for the Purpose of Patent Procedure, on Apr. 16, 2002, at American Type Culture Collection (ATCC), University Blvd., Manassas, Va. 20110-2209, USA and having the designation PTA-4233.

As used herein, *Delftia acidovorans* RAY209 means a strain of *Delftia acidovorans* deposited in accordance with the Budapest Treaty on the International Recognition of the Deposit of Microorganisms for the Purpose of Patent Procedure, on Apr. 25, 2002, at American Type Culture Collection (ATCC), 10801 University Blvd., Manassas, Va. 20110-2209, USA and having the designation PTA-4249.

As used herein, "biologically pure" refers to a culture wherein virtually all of the cells present are of the selected strain.

As used herein, "inoculating" refers to introducing at least one bacterium into a medium, for example, a liquid medium, peat powder, seed or a soil environment.

As used herein, "PGPR" or "plant growth-promoting rhizobacteria" refers to plant-beneficial isolates which inhabit the area surrounding plant roots.

As used herein, "soil environment" refers to the soil in which a plant is grown or is growing.

As will be appreciated by one of skill in the art, as used herein, "sulfur-oxidizing PGPR" refers to beneficial bacterial cultures and isolates as well as cell extracts (extracellular or intracellular) or enzymes purified or isolated therefrom derived therefrom capable of oxidizing sulfur, promoting sulfur uptake, improving plant growth and/or improving plant yield.

Described herein is the isolation and identification of a number of sulfur oxidizing plant growth promoting rhizobacteria: RAY12, identified as *Achromobacter piechaudii*; RAY28, identified as *Agrobacterium tumefaciens*, RAY132, identified as *Stenotrophomonas maltophilia*; and RAY209, identified as *Delftia acidovorans*. As discussed below, these PGPR act to oxidize sulfur and thereby provide sulfate for plants. As a result of this arrangement, plants are able to grow more efficiently and effectively and thereby have enhanced growth characteristics, for example, but by no means limited to, increased vigor, early emergence, increased emergence rate, increased biomass, increased plant leaf area, higher crop yield, increased pod number, increased pod weight, increased root biomass, increased seed weight, increased sulfur uptake as well as increasing the uptake of other macro- and micronutrients and the like. As discussed below, the sulfur-oxidizing PGPR may be applied to seeds, seed pieces, carrier materials, roots and planting soil. For example, the sulfur-oxidizing PGPR may be coated onto a seed or seed piece, may be applied as a powder or as a suspension to a soil environment or may be mixed into a soil environment prior to use of the soil environment for planting.

In the examples, the plant is canola which, as discussed above, is a high-sulfur demanding crop. As will be apparent to one knowledgeable in the art, the sulfur-oxidizing PGPR described herein may be used to promote growth of any suitable plant, for example root plants for example sugar beets, potatoes, radishes and the like; cereals for example oat, barley and the like; forages for example alfalfa and the like; oil seeds for example canola, hemp and sunflower. That is, the sulfur-oxidizing PGPR may promote growth of all suitable plants having high sulfur requirement.

Similarly, in some embodiments of the invention, the sulfur-oxidizing PGPR are used in a soil environment which has low levels of sulfur. It is of note that, as discussed above, the sulfur-oxidizing PGPR can be used in any suitable soil conditions as the presence of the sulfur-oxidizing PGPR will promote more efficient usage of sulfur by plants grown in a soil environment and will thereby promote growth of plants grown in the soil environment. Thus, the above-described PGPR are capable of oxidizing elemental S to thiosulfate; capable of oxidizing thiosulfate to sulfate; capable of oxidizing elemental S to sulfate; capable of oxidation of elemental form of sulfur; promoting S-uptake in plants; capable of alleviating a S-deficiency in plant; and capable of alleviating S-deficiency in S-deficient soil fertilized with elemental S.

In yet other embodiments, the sulfur-oxidizing PGPR may be applied to a soil environment which has been or will be treated with a sulfur-containing fertilizer, for example, elemental sulfur. It is also of note that the sulfur-oxidizing PGPR may promote uptake of sulfur and other macro- and micro-nutrients within the soil environment whether provided by a fertilizer or not.

In other embodiments, the sulfur-oxidizing PGPR are in combination with a carrier. The carrier may be a pellet, granular mass, peat pellet, perlite granule or other similar element or may be a plant seed. Specifically, the sulfur-oxidizing PGPR may be coated onto a seed using means known in the art. As way of example, the sulfur-oxidizing PGPR may be mixed with peat, clay, polymer or agriculturally compatible oil. In other embodiments, the sulfur-oxidizing PGPR may be lyophilized or freeze-dried to a powder or an aqueous slurry of the sulfur-oxidizing PGPR may be dried to a powder at a temperature which does not adversely affect viability of the micro-organism. The powder may then be mixed with peat, clay, talc or other earth materials. In yet other embodiments, a liquid suspension of the sulfur-oxidizing PGPR may be used to coat the seeds or applied to an absorbent material, for example, a granular material.

As will be appreciated by one of skill in the art, bacterial viability is one of the most important factors for successful and adequate colonization of the rhizosphere and rhizoplane that ultimately affects plant performance and yield. As such, specific soil conditions and growth temperature which may vary greatly from site to site influence bacterial viability and therefore plant yield. Thus, while RAY12, identified as *Achromobacter piechaudii*; RAY28, identified as *Agrobacterium tumefaciens*, RAY132, identified as *Stenotrophomonas maltophilia*; and RAY209, identified as *Delftia acidovorans*; are all individually effective at promoting plant growth as described herein, in some embodiments, mixtures of any or all of the sulfur-oxidizing PGPR may be used in the embodiments of the invention described herein. It is also of note that some combinations may work better under specific conditions, such as soil pH, growth temperature, time of planting, and plant type or species. These combinations are within the scope of the invention.

As will be appreciated by one of skill in the art, the sulfur-oxidizing PGPR or mixtures thereof may be combined with other suitable pesticidal agents, for example, fungicides or other PGPR and used in the embodiments described herein. That is, combining the sulfur-oxidizing PGPR with biocontrol PGPR or fungicides may further enhance plant growth as pathogens would be reduced. Similarly, combining the above-described sulfur-oxidizing PGPR with other plant growth-promoting PGPR may have a synergistic effect in promoting plant growth. It is of note that these combinations may be used in any of the above-described embodiments, for example, for coating seeds.

In yet other embodiments of the invention, the sulfur oxidizing plant growth promoting rhizobacteria: RAY12, identified as *Achromobacter piechaudii*; RAY28, identified as *Agrobacterium tumefaciens*, RAY132, identified as *Stenotrophomonas maltophilia*; and RAY209, identified as *Delftia acidovorans*; or mixtures thereof are used as biocontrol agents or as biofungicides. As will be appreciated by one knowledgeable in the art, in these embodiments, the above-described PGPR is applied in any of the ways described above, and promotes plant growth by acting as a biocontrol agent or biofungicide. In yet other embodiments, the above-described PGPR is applied to a soil environment either alone or in combination with a compatible fungicide such that the amount of fungicide used is reduced. For example, in some embodiments, an agriculturally compatible carrier, for example, a seed, may be coated with the above-described PGPR and a compatible fungicide.

The invention will now be described by way of examples. However, it is to be understood that the examples are for illustrative purposes and the invention is not limited to the examples.

EXAMPLE 1

Sulfur-Oxidizing Rhizobacteria Isolation

Presumptive S-oxidizing rhizobacteria were isolated by plating serial dilution of the canola rhizosphere soil and rhizoplane (Grayston and Germida, 1991). The TSA (trypticase soy agar, $\frac{1}{10}$ strength) media was used as the laboratory basal media. Laboratory modified two enrichment sulfur media were used for presumptive S-oxidizing bacterial isolation purpose. The thiosulphate and flowable elemental sulfur (FS) were used as suitable S source in the two different media. Flowable sulfur (Stoller Enterprises, Inc., Houston) is a brownish yellow colored creamy liquid with impurities and contains approximately 52% of elemental S. The FS was cleaned with distilled water. This FS was added to the media to provide the final concentration of 0.2% S in the solid media (i.e. TSA) and 1% S in the liquid media (i.e. trypticase soy broth, TSB). In the media bromothymol blue indicator was also used to record the change in media pH. Media plates were examined carefully daily and streaked several times (as needed) onto solidified media of the same composition for obtaining pure culture of rhizobacteria. While oxidizing sulfur, bacteria produce sulphuric acid and thus lower the pH of the media.

In-Vitro Sulfur Oxidation:

To examine the S-oxidizing ability of the bacterial isolates, in vitro S-oxidation was measured qualitatively (Grayston and Germida, 1990; Banerjee, 1995). Polystyrene, non-pyrogenic, sterile cell culture cluster was used as microtiter plates/wells for this test. Laboratory modified sulfur enrichment liquid media and basal media without S source were used in the microtiter plates. Each isolate was grown overnight in TSB ($\frac{1}{10}^{th}$ strength). These overnight cultures (0.1 ml) were inoculated to each well. Control wells of microtiter plates containing each medium were included to detect false positive results. The plates were wrapped in polyethylene bags and incubated at 28° C. for approximately two weeks. The initial visual color change of the media helped to find S-oxidizing bacteria in most of the cases. However, some bacteria could produce acid without the presence of S-source. Therefore, a chemical confirmatory test was conducted to test for sulfate and thiosulphate production as in the presence of elemental sulfur, thiosulphate and tetrathionate are the two main intermediate forms of sulfur produced during the oxidation of elemental sulfur to sulfate. A colorimetric determination of thiosulphate and tetrathionate method was used to score the wells positive or negative for thiosulphate/tetrathionate production (Nor and Tabatabai, 1976, *Soil Science* 122: 171-178). The intensity of the color produced shown the capability of sulfur oxidation. Some bacteria transformed elemental sulfur to thiosulphate, some were responsible for tetrathionate production from thiosulphate (although tetrathionate production was found to be very low) and others were capable of producing sulphate from sulfur. In the test production of sulfate was tested turbidimetrically (Hesse, 1971, A Textbook of Soil Chemical Analysis) by adding a spatula of $BaCl_2$ to each well.

Out of a total of 419 presumptive sulfur-oxidizing bacterial strains isolated from the canola rhizosphere and rhizoplane four rhizobacterial strains RAY12, RAY28, RAY132 and RAY209 were found positive to producing thiosulfate or tetrathionate from elemental S, thiosulfate to sulfate, elemental S to sulfate, and also from elemental S and thiosulfate to sulfate (Table 1).

EXAMPLE 2

Quantitative Test of Sulfur Oxidation

For the determination of quantitative bacterial S-oxidation an incubation study was set with all of the four strains in TSB with a known amount of elemental S at 28° C. for a period of up to 100 days. Production of sulfate sulfur from the elemental sulfur were measured at 0, 10, 20, 30, 40, 60, 80 and 100 day intervals (FIG. 1). The capabilities of sulfur oxidation by the strains RAY12, RAY28, RAY132 and RAY209 can also be seen in Table 2. It is interesting to note that RAY12, RAY132 and RAY209 oxidize 30-48% of elemental sulfur between 30 and 60 days when the canola plant needs the sulfur most.

EXAMPLE 3

Seed Germination/Emergence Test

Herbicide-tolerant cultivar 799RR canola seed were surface sterilized for bacterial inoculation. Bacteria were grown in TSB for 48 hours and harvested by centrifugation. Bacterial numbers were determined by plating serial dilution of that washed cell cultures on TSA plates. Surfaced sterilized canola seeds were inoculated with the appropriate washed bacterial cultures and spread on to TSA plates to examine the effect on seed germination (Table 3). Sets of uninoculated seeds were also spread on the TSA plates as control (Table 3). Besides agar plates, seed germination and/or emergence test was also done in soil (Table 4) as well as using growth pouch (Table 5). Results indicated that none of the rhizobacterial isolates inhibited canola seed germination (Table 3). However, the bare canola seeds inoculated with bacterial isolates seem to accelerate germination time compared to control (Table 4 and Table 5).

EXAMPLE 4

Survivability of Bacterial Isolates on Seed and in Carrier Materials

The success of microbial inoculation for enhanced crop production is greatly influenced by the number of viable cells introduced into soil (Duquenne et al., 1999) as well as biological activity may also decline rapidly with handling and storage procedure if not properly done. Thus, it is crucial to determine the duration of bacterial survivability after the bacterial seed treatment and to obtain the desired level of microbial population for the inoculant to be effective. Inoculated bare seed showed desirable viable cell count up to about 11 days after inoculation (Table 6). It is known that coating of seed may increase the bacterial survivability as coating of bacteria treated canola seeds seals bacteria onto the seeds and prevents cells from drying out and keeps bacteria alive much longer than bare seeds. From the laboratory observation it was found that canola seeds coated with peat-clay mixture had increased bacterial survivability between 20-29 days with viable cell count of 3-8 cfu×$10^5$ per seed. The coated seeds were also checked for their seed germination capability (Table 5) and coated seeds showed slower initial germination compared to the bare seeds.

In order to obtain effective rhizobacterial inoculants, screened isolates were tested for their viability and shelf life with different inoculant carrier materials. Isolates were grown in sterile trypticase soy broth (TSB) for 48 hours and isolates grown in broth solutions were used directly to inoculate commercially available carrier materials such as gamma irradiated sterilized peat powder and granular carrier material. These carrier materials were tested for bacterial survivability at different time intervals. It is shown that when sterile peat bags were inoculated with the rhizobacterial strains RAY12, RAY28, RAY132 and RAY209 survivability of the strains were increased up to 150 days at over $10^8$ cfu per gram of carrier material (Table 7). It was also observed in the laboratory that when the bacterial cells harvested by centrifugation from the TSB broth were freeze-dried and kept at 22° C., bacterial viability remained virtually unchanged. Similarly when bacterial suspensions were sprayed on peat based granules, bacterial strains remained viable.

EXAMPLE 5

Growth Pouch Experiment for Plant Growth Promotion (PGP) Test

Canola seeds inoculated with screened rhizobacterial strains were germinated in sterile growth pouch at 22° C.±2. A set of control seed was also germinated under similar conditions. After 7 days, hypocotyl and roots lengths were measured. Visual presentation and data are shown in FIGS. 2, 3 and 4. At 7 days, growth promotion was observed in hypocotyl and root length after canola seeds inoculated with PGPR strains RAY12, RAY28, RAY132 and RAY209. All of these bacterial strains enhanced the root and hypocotyls growth significantly in comparison to uninoculated control.

EXAMPLE 6

Growth Room Experiment Using Screened Rhizobacterial Isolates for PGP Test

Effects of bacterial inoculation on plant growth parameters were studied in a growth room with the four screened S-oxidizing strains (RAY12, RAY28, RAY132 and RAY209). More emphasis was given on plant growth characteristics including canola seed yield. Growth room assay was conducted with a sulfur deficient field soil, collected near Melfort, Saskatchewan, and was a loam (pH 7.8, electrical conductivity (mS/cm) 0.2 with following nutrient levels in ppm: nitrate nitrogen 7.3, phosphorous 14.6, potassium 187.1 and sulfur 9.5. Rhizobacterial strains RAY12, RAY28, RAY132 and RAY209 were used for the canola seed inoculation. The experiment was consisting of eight bacterial treatments along with three controls (control—no sulfur; elemental S control; and sulfate S control) each having three replications. One and half kg sieved soil (<5 mm mesh) was added to 16-cm plastic pots and the pots were kept in a growth room (22° C., 16 h light; 18° C., 8 h dark). Five seeds were planted in each of the pots and seedlings were thinned to one per pot after emergence. Daily watering to constant weight ensured similar matric potential between the pots. Canola plants were harvested at maturity (105 DAP) and stalk dry weight, pod number, pod weight and seed weight or yield determined. In another growth room experiment done in similar manner as previous one, canola seed yield, and, seed macronutrients (S, N, P, K, Ca and Mg) and micronutrients (Zn, B, Cu and Fe) uptake were determined.

All the bacterial isolates in general increased the canola plant biomass and yield (Table 8). Bacterial inoculation along with elemental S application in general showed higher seed yield compared to controls. For example, with elemental S application RAY12, RAY28, RAY132 and RAY209 increased canola seed yield by 103%, 48%, 79% and 100% respectively, over the combined mean of the controls (Table 8). Whereas bacterial inoculation of RAY12, RAY28, RAY132 and RAY209 alone increased canola seed yield by 16%, 27%, 57% and 90% respectively, over the combined mean of the controls. These strains even showed higher or similar effect in comparison to sulfate sulfur control although sulfate sulfur was the reference control revealing their capability of enhancing canola growth and performance. Inoculation of canola seeds with the strains RAY12, RAY28, RAY132 and RAY209 enhanced the seed yield as well as the sulfur uptake in comparison to controls in another experiment (Table 9). The increase in S uptake was more pronounced in the presence of elemental sulfur (ES). For example, Bacteria plus elemental S treatment on an average increased 52.6% S uptake over the on an average control treatment, whereas bacteria treatment alone on an average increased 38.9% S uptake over the on an average control treatment. Thus, it appears that enhanced S-oxidation by the bacterial strains is at least in part an important mechanism for growth promotion in Canola. As the increase in S uptake may have been due to the increased availability of sulfate in soil through the oxidation of elemental sulfur to sulfate. Moreover, Table 9 also revealed that in addition to the increment of uptake of specific nutrient like S, these PGPR strains might have stimulated uptake of other macro—(N, P, K, Ca and Mg) and micronutrients (Zn, B, Mn and Cu) in general. These impacts could be due to the production of phytohormones by the microorganisms (de Freitas and Germida, 1990, *Canadian Journal of Microbiology* 36: 265-272), and might also be explained by increased availability brought on by the acidification process associated with S-oxidation as well as the larger root systems.

EXAMPLE 7

Fungicide Compatibility Test

In the Canadian prairies, at present fungicide Helix (Syngenta Canada Inc.) is commonly used with canola seeds as pre-seeding seed treatment. As environmental concerns are increasing about using pesticides in agriculture, biological alternatives seem inevitable (Walter and Paau, 1997). However, new biological formulations must also allow organisms to survive and express their specific beneficial impact. Chemical fungicides are generally toxic not only towards deleterious microorganisms but also to the beneficial ones. In an experiment, Vitavax RS (contains carbathin+thiram+lindane) when applied at recommended dose showed high toxicity towards beneficial rhizobacteria (Yesmin and Banerjee, 2000). However, chance of survivability of these microbial agents might have been enhanced when applied at reduced rates (Yesmin and Banerjee, 2001). In the present study, peat-based carrier material was used for inoculation of both the fungicide treated as well as bare canola seed. Bacterial tolerability of fungicide Helix was evaluated in the following manner: a) bacteria inoculated bare seeds grown on Helix enriched trypticase soy agar (TSA) plates, b) Helix treated bacteria inoculated canola seeds grown on common TSA plates, and, c) Helix treated bacteria inoculated canola seeds grown in the sterile growth pouches. Three rates of Helix were used in the experiment, recommended dose (H15; 15 ml/kg seed) and two lower doses (H10; 10 ml/kg seed and H5; 5 ml/kg seed). Helix treated bacteria inoculated seeds were kept after inoculation and used at different time intervals (2 hrs, 4 hrs and 6 hrs) to examine the impact on seed germination. Both seed germination and bacterial presence were observed in petri-plates. For the growth pouch study, Helix treated (recommended dose) canola seeds were used, and root and hypocotyl lengths were measured at 7 days of canola growth.

Present investigations have shown that all of the rhizobacterial strains RAY12, RAY28, RAY132 and RAY209 are compatible with Helix (contains thiamethoxam+difenoconazole+metalaxyl-M+fludioxonil) and grow on Helix enriched TSA plates. Both bare and Helix treated seeds, coated with inoculated peat showed no variation in germination compared to uninoculated control (Table 10). The general recommendation for any microbial inoculants is to seed soon after seed inoculation. When Helix treated seeds were coated with peat inoculants and kept for 6 hours, no variation in seed germination was found either with time intervals or fungicides doses in petri plates (Table 10). Visual observations showed presence of rhizobacteria in all of the inoculated treatments. Recommended dose (H15) of Helix treated inoculated seeds showed no inhibition on seed germination or on plant growth. Moreover, growth-promoting effects on root and total plant lengths were observed in all rhizobacterial treatments compared to control in the growth pouches (FIG. 5).

EXAMPLE 8

Field Trials Using Screened Rhizobacterial Isolates

In 2001, field trials were carried out using four canola PGPR strains. The canola trials were planted through commercial seed planter using bacterial inoculated peat-clay coated seeds. The cultivar used was herbicide-tolerant 799RR, All field trials were split-spilt block design of each plot size of 6 m×1.5 m, with eight bacterial treatments along with one control, all with four replicates. The treatments were designed to evaluate bacterial ability to enhance canola yield with or without elemental sulfur in comparison with control (sulfate sulfur treatment). Plots were harvested at maturity, seed was collected and cleaned, and yield was measured based on 8.5% seed moisture. Canola yield data in Miami, MB, site were presented in FIG. 6. FIG. 6 showed that the PGPR+ES treatment on an average increased canola yield by 35% over the sulfate sulfur control, whereas, the PGPR treatment alone on an average increased canola yield by 9% over the sulfate sulfur control.

In 2002, field trials were carried out using three canola PGPR strains. The canola trials were planted through commercial seed planter using bacteria inoculated powdered peat-based carrier material coated seeds. The cultivar used was the same as 2001. All field trials were randomized complete block design having each plot size of 6 m×1.5 m, with nine bacterial treatments along with three controls, all with six replicates. The treatments were designed to evaluate bacterial ability to enhance canola yield with or without elemental sulfur in comparison with controls (no sulfur, elemental sulfur and sulfate sulfur). Plots were harvested at maturity, seed was collected and cleaned, and yield was measured based on 8.5% seed moisture. In addition, canola seed macronutrients (S, N, P, K, Ca and Mg) and micronutrients (Zn, Mn, Cu and Fe) uptake were also determined. Canola yield data and seed nutrients uptake in Dauphin, MB, site were presented in FIG. 7 and Table 11. FIG. 7 showed that the PGPR+ES treatment on an average increased canola yield by 12.7% over the no sulfur control and 14.7% over the elemental sulfur control. Moreover, PGPR+ES treatment virtually achieved the similar yield as the sulfate sulfur control, whereas the PGPR treatment alone on an average increased canola yield by 11.5% over the no sulfur control and 13.5% over the elemental sulfur control. Inoculation of canola seeds with the strains RAY12, RAY132 and RAY209 not only enhanced the canola yield but also enhanced the sulfur uptake in canola seeds with and without ES in comparison to control and control+ES in the field (Table 11). For example, RAY132 treatment increased S uptake by 19.6% over the control treatment and RAY132+ES treatment increased S uptake by 21.6% over the control+ES treatment. Thus, it suggests that enhanced S-oxidation carried out by the bacterial strains enhances the available sulfur level for plant to take up that aids in growth promotion effect in Canola. In fact, S uptake had been increased because of the bacterial inoculation and almost comparable to the level of sulfate sulfur control (Table 11). Moreover, Table 11 also revealed that in addition to the increment of S uptake, these PGPR strains might have also stimulated uptake of other macro—(N, P, K, Ca and Mg) and micro-nutrients (Zn, Mn, Cu and Fe) in general.

EXAMPLE 9

Bacterial Characterization and Identification

The bacterial strains RAY12, RAY28, RAY132 and RAY209 are soil bacteria associated with the plant rhizosphere. The optimum temperature requirements for these strains are 28-30° C., but they can also grow at slower rate at lower (e.g., 10° C.) and higher (e.g., 36° C.) temperature. The TSB is generally used in the laboratory for their mass culturing. Table 12 shows the other important characteristics of these PGPR strains.

For identification purposes, the bacterial strains (RAY12, RAY28, RAY132 and RAY209) were grown on TSA media for 48 hours. Then the bacterial DNA was extracted from the bacterial strains for 16S rRNA and 500 bp (base pair) identification using the services of MIDI LABS (Newark, Del.). The strains were identified as *Achromobacter piechaudii*

RAY12, *Agrobacterium tumefaciens* RAY28, *Stenotrophomonas maltophilia* RAY132 and *Delftia acidovorans* RAY209.

While the preferred embodiments of the invention have been described above, it will be recognized and understood that various modifications may be made therein, and the appended claims are intended to cover all such modifications which may fall within the spirit and scope of the invention.

TABLE 1

Sulfur-oxidizing bacteria isolated from the rhizosphere and rhizoplane of canola

| SITE | AREA OF ISOLATION | SCREENED ISOLATE | NO. OF ISOLATES PRODUCING | | | |
|---|---|---|---|---|---|---|
| | | | $S^0 \rightarrow S_2O_3^{2-}/S_4O_6^{2-}$ | $S_2O_3^{2-} \rightarrow SO_4^{2-}$ | $S^0 \rightarrow SO_4^{2-}$ | $S^0 \rightarrow S_2O_3^{2-} \rightarrow SO_4^{2-}$ |
| GP1 | Rhizoplane | RAY12 | + | + | + | + |
| | | RAY28 | + | + | + | + |
| MF | Rhizosphere | RAY132 | + | + | + | + |
| GP3 | Rhizoplane | RAY209 | + | + | + | + |

TABLE 2

Elemental sulfur oxidation by rhizobacterial strains

| BACTERIAL ISOLATE | % SULFUR OXIDIZED | | | | | | |
|---|---|---|---|---|---|---|---|
| | 10 DAY | 20 DAY | 30 DAY | 40 DAY | 60 DAY | 80 DAY | 100 DAY |
| RAY12 | 13.51 ± 0.87 | 28.58 ± 1.66 | 30.41 ± 0.77 | 36.25 ± 3.61 | 41.48 ± 2.15 | 43.40 ± 4.18 | 44.91 ± 3.06 |
| RAY28 | 0.00 | 0.00 | 6.58 ± 2.01 | 13.00 ± 3.61 | 23.79 ± 2.05 | 37.12 ± 3.91 | 51.25 ± 8.74 |
| RAY132 | 16.58 ± 0.29 | 22.56 ± 1.10 | 31.96 ± 4.11 | 38.67 ± 3.51 | 47.69 ± 4.70 | 85.67 ± 1.76 | 98.85 ± 0.51 |
| RAY209 | 19.58 ± 1.93 | 31.06 ± 2.47 | 35.20 ± 4.71 | 35.56 ± 3.18 | 42.41 ± 3.22 | 94.08 ± 4.03 | 99.40 ± 0.42 |

TABLE 3

Seed germination upon rhizobacterial inoculation in agar plate

| INOCULATION TREATMENT | DAY 3 (%) | DAY 5 (%) | DAY 7 (%) |
|---|---|---|---|
| Surface sterilized control | 99 | 99 | 99 |
| RAY12 | 100 | 100 | 100 |
| RAY28 | 100 | 100 | 100 |
| RAY132 | 100 | 100 | 100 |
| RAY209 | 99 | 99 | 99 |

TABLE 4

Seed emergence in soil upon rhizobacterial inoculation

| INOCULATION TREATMENT | DAY 3 (%) | DAY 5 (%) | DAY 7 (%) | DAY 10 (%) |
|---|---|---|---|---|
| Surface sterilized control | 60 | 82 | 94 | 94 |
| Helix treated control | 54 | 90 | 90 | 92 |
| Foundation treated control | 30 | 76 | 80 | 86 |
| RAY12 | 90 | 96 | 96 | 96 |
| RAY28 | 80 | 90 | 94 | 94 |
| RAY132 | 92 | 96 | 96 | 96 |
| RAY209 | 88 | 92 | 94 | 94 |

TABLE 5

Seed germination upon rhizobacterial inoculation in growth pouch

| INOCULATION TREATMENT | COATING TREATMENT | DAY 3 (%) | DAY 5 (%) | DAY 7 (%) |
|---|---|---|---|---|
| Surface sterilized control | Non-coated | 90.0 | 90.0 | 90.0 |
| | Coated | 77.5 | 77.5 | 87.5 |
| RAY12 | Non-coated | 97.5 | 97.5 | 97.5 |
| | Coated | 92.5 | 95.0 | 95.0 |
| RAY28 | Non-coated | 90.0 | 90.0 | 90.0 |
| | Coated | 92.5 | 92.5 | 92.5 |
| RAY132 | Non-coated | 92.5 | 95.0 | 95.0 |
| | Coated | 82.5 | 92.5 | 92.5 |
| RAY209 | Non-coated | 92.5 | 92.5 | 92.5 |
| | Coated | 80.0 | 87.5 | 90.0 |

TABLE 6

Viability of bacterial strains (cfu × $10^5$ per seed) after inoculation of bare canola seed

| INOCULATION TREATMENT | SEED WASH TREATMENT | DAY 4 | DAY 11 | DAY 21 |
|---|---|---|---|---|
| Surface sterilized control | Washed | 0 | 0 | 0 |
| | Non-washed | 0 | 0 | 0 |
| RAY12 | Washed | 11 | 8 | 6 |
| | Non-washed | 3 | 1 | 0 |
| RAY28 | Washed | 19 | 11 | 5 |
| | Non-washed | 4 | 2 | 1 |
| RAY132 | Washed | 52 | 23 | 8 |
| | Non-washed | 5 | 3 | 2 |

TABLE 6-continued

Viability of bacterial strains (cfu × $10^5$ per seed) after inoculation of bare canola seed

| INOCULATION TREATMENT | SEED WASH TREATMENT | DAY 4 | DAY 11 | DAY 21 |
|---|---|---|---|---|
| RAY209 | Washed | 13 | 8 | 4 |
|  | Non-washed | 3 | 1 | 0 |

TABLE 7

Bacterial survivability in powdered peat carrier material

| BACTERIAL STRAIN | INCUBATION PERIOD (DAY) | CFU/G OF CARRIER |
|---|---|---|
| RAY12 | 33 | >$10^9$ |
|  | 46 | 3 × $10^8$ |
|  | 67 | >$10^9$ |
|  | 87 | >$10^9$ |
|  | 104 | >$10^9$ |
|  | 127 | >$10^9$ |
|  | 150 | 1 × $10^8$ |
| RAY28 | 33 | >$10^9$ |
|  | 46 | >$10^9$ |
|  | 67 | >$10^9$ |
|  | 87 | >$10^9$ |
|  | 104 | >$10^9$ |
|  | 127 | >$10^9$ |
|  | 150 | 2 × $10^8$ |
| RAY132 | 33 | >$10^9$ |
|  | 46 | >$10^9$ |
|  | 67 | >$10^9$ |
|  | 87 | >$10^9$ |
|  | 104 | >$10^9$ |
|  | 127 | >$10^9$ |
|  | 150 | >$10^9$ |
| RAY209 | 33 | >$10^9$ |
|  | 46 | >$10^9$ |
|  | 67 | >$10^9$ |
|  | 87 | >$10^9$ |
|  | 104 | >$10^9$ |
|  | 127 | >$10^9$ |
|  | 150 | >$10^9$ |

TABLE 8

Biomass and yield of canola plants at 105 DAP inoculated with S-oxidizing rhizobacteria grown in Melfort, SK soil

| TREATMENT | STALK DRY WT. (G/PLANT) | POD NO. (NO./PLANT) | POD WT. (G/PLANT) | SEED WT. (G/PLANT) |
|---|---|---|---|---|
| Control | 4.15 | 72 | 4.52 | 1.77 |
| Control + ES | 3.84 | 58 | 3.17 | 1.13 |
| Control + SO$_4$ | 4.56 | 78 | 4.20 | 1.71 |
| Control + RAY12 | 5.87*** | 79 | 4.25 | 1.79 |
| Control + RAY28 | 5.35* | 88 | 4.81 | 1.96 |
| Control + RAY132 | 5.26* | 86 | 4.95 | 2.42* |
| Control + RAY209 | 4.50 | 93** | 5.84** | 2.94*** |
| Control + ES + RAY12 | 4.74 | 89* | 6.05** | 3.13*** |
| Control + ES + RAY28 | 5.03 | 82 | 5.14 | 2.29 |
| Control + ES + RAY132 | 5.12 | 94** | 5.70* | 2.76** |
| Control + ES + RAY209 | 4.96 | 95** | 6.19** | 3.08*** |
| LSD |  |  |  |  |
| 10% | 1.04 | 17 | 1.09 | 0.62 |
| 5% | 1.25 | 20 | 1.31 | 0.75 |
| 1% | 1.70 | 28 | 1.78 | 1.02 |

N.B. *, , *means treatments are significantly different from control at P < 0.001, P < 0.05 and P < 0.01, respectively.

TABLE 9

Per plant basis seed yield, macronutrient uptake and micronutrient uptake of canola plants inoculated with S-oxidizing rhizobacteria in growth room experiment

| Treatment | Seed yield (g) | S uptake (mg) | N uptake (mg) | P uptake (mg) | K uptake (mg) | Ca uptake (mg) | Mg uptake (mg) | Zn uptake (µg) | B uptake (µg) | Mn uptake (µg) | Cu uptake (µg) |
|---|---|---|---|---|---|---|---|---|---|---|---|
| Control | 2.13 | 11.50 | 86.79 | 20.65 | 23.36 | 8.31 | 8.43 | 1.49 | 0.15 | 0.94 | 0.03 |
| Control + ES | 2.92 | 18.66 | 116.30 | 28.71 | 28.42 | 12.10 | 11.37 | 2.08 | 0.09 | 1.14 | 0.03 |
| Control + SO$_4$ | 3.11 | 15.76 | 116.30 | 28.24 | 27.52 | 11.71 | 12.12 | 1.72 | 0.13 | 1.22 | 0.03 |
| Control + RAY12 | 3.79 | 21.23 | 141.20 | 33.09 | 34.96 | 12.84 | 14.91 | 2.01 | 0.14 | 1.39 | 0.03 |
| Control + RAY28 | 4.14 | 18.79 | 152.50 | 37.79 | 37.61 | 16.28 | 16.79 | 2.15 | 0.16 | 1.48 | 0.03 |
| Control + RAY132 | 4.26 | 25.62 | 158.40 | 37.56 | 38.52 | 17.70 | 16.72 | 2.37 | 0.17 | 1.63 | 0.03 |
| Control + RAY209 | 4.26 | 19.38 | 166.00 | 37.37 | 35.37 | 15.86 | 17.34 | 2.36 | 0.17 | 1.59 | 0.05 |
| Control + ES + RAY12 | 4.23 | 29.61 | 174.70 | 40.61 | 48.22 | 14.81 | 16.29 | 2.04 | 0.16 | 1.50 | 0.03 |
| Control + ES + RAY28 | 3.88 | 23.07 | 152.00 | 34.42 | 38.53 | 15.05 | 15.14 | 2.14 | 0.17 | 1.37 | 0.04 |

TABLE 9-continued

Per plant basis seed yield, macronutrient uptake and micronutrient uptake of canola plants inoculated with S-oxidizing rhizobacteria in growth room experiment

| Treatment | Seed yield (g) | S uptake (mg) | N uptake (mg) | P uptake (mg) | K uptake (mg) | Ca uptake (mg) | Mg uptake (mg) | Zn uptake (μg) | B uptake (μg) | Mn uptake (μg) | Cu uptake (μg) |
|---|---|---|---|---|---|---|---|---|---|---|---|
| Control + ES + RAY132 | 4.03 | 18.33 | 141.60 | 37.14 | 37.32 | 14.58 | 15.84 | 2.14 | 0.16 | 1.37 | 0.04 |
| Control + ES + RAY209 | 3.83 | 22.41 | 132.30 | 34.09 | 42.71 | 12.82 | 13.98 | 2.20 | 0.22 | 1.37 | 0.04 |

TABLE 10

Helix treated seed germination in agar plates upon rhizobacterial inoculation

| INOCULATION TREATMENT | HELIX DOSE (ML/KG SEED) | 2 HOURS (%) | 4 HOURS (%) | 6 HOURS (%) |
|---|---|---|---|---|
| Control | 0 | 100 | 100 | 100 |
|  | 5 | 93 | 100 | 100 |
|  | 10 | 100 | 100 | 100 |
|  | 15 | 100 | 95 | 95 |
| RAY12 | 0 | 97 | 100 | 100 |
|  | 5 | 100 | 100 | 100 |
|  | 10 | 100 | 100 | 100 |
|  | 15 | 93 | 95 | 100 |
| RAY132 | 0 | 100 | 97 | 100 |
|  | 5 | 97 | 100 | 100 |
|  | 10 | 100 | 95 | 100 |
|  | 15 | 97 | 100 | 95 |
| RAY209 | 0 | 97 | 100 | 100 |
|  | 5 | 100 | 100 | 100 |
|  | 10 | 100 | 100 | 100 |
|  | 15 | 97 | 97 | 100 |

TABLE 11

Seed macronutrient and micronutrient uptake of canola plants inoculated with S-oxidizing rhizobacteria in Dauphin field site

| Treatment | S uptake (kg/ha) | N uptake (kg/ha) | P uptake (kg/ha) | K uptake (kg/ha) | Ca uptake (kg/ha) | Mg uptake (kg/ha) | Zn uptake (g/ha) | Mn uptake (g/ha) | Cu uptake (g/ha) | Fe uptake (g/ha) |
|---|---|---|---|---|---|---|---|---|---|---|
| Control | 4.25 | 33.75 | 7.74 | 7.60 | 4.64 | 3.61 | 42.49 | 29.62 | 2.08 | 55.65 |
| Control + ES | 4.13 | 32.91 | 7.54 | 7.60 | 4.50 | 3.51 | 40.05 | 28.97 | 2.17 | 57.17 |
| Control + SO₄ | 5.10 | 39.74 | 8.71 | 9.09 | 5.02 | 4.14 | 51.32 | 37.22 | 2.61 | 68.20 |
| Control + RAY12 | 4.81 | 39.97 | 8.97 | 8.79 | 5.27 | 4.11 | 49.75 | 35.01 | 2.22 | 62.98 |
| Control + RAY132 | 4.94 | 39.58 | 8.43 | 8.49 | 4.97 | 3.98 | 49.34 | 34.94 | 2.28 | 63.38 |
| Control + RAY209 | 4.83 | 38.60 | 8.72 | 8.78 | 5.05 | 4.00 | 45.52 | 33.8 | 2.31 | 59.65 |
| Control + ES + RAY12 | 4.84 | 38.99 | 8.41 | 8.71 | 4.87 | 3.99 | 49.47 | 34.77 | 2.30 | 62.54 |
| Control + ES + RAY132 | 5.02 | 40.23 | 8.80 | 8.89 | 5.18 | 4.13 | 49.58 | 35.94 | 2.52 | 64.89 |
| Control + ES + RAY209 | 4.84 | 38.53 | 9.21 | 8.78 | 5.26 | 4.10 | 46.68 | 34.07 | 2.00 | 59.37 |

TABLE 12

Characterization of different PGPR strains

| Biochemical substrate utilization and other characteristics | Bacterial species | | | |
|---|---|---|---|---|
| | *Achromobacter piechaudii* RAY12 | *Agrobacterium tumefaciens* RAY28 | *Stenotrophomonas maltophilia* RAY132 | *Delftia acidovorans* RAY209 |
| Gram staining | Gram negative | Gram negative | Gram negative | Gram negative |
| Shape | Small rod | Rod | Rod | Rod |
| Catalase test | + | − | − | + |
| Cytochrome oxidase | + | nd | − | + |
| Inositol | − | − | − | − |
| Glucose | + | − | − | − |
| Lactose | − | − | − | − |
| Sucrose | − | − | − | nd |
| Citrate | + | + | + | + |
| Lysine decarboxylase | − | − | − | − |
| Ornithine decarboxylase | − | − | − | − |
| Arginine decarboxylase | − | − | − | − |
| Gelatin liquefaction | + | − | + | − |
| Esculin hydrolysis | + | + | + | + |
| Hydrogen sulfide production | − | − | − | − |
| Indole test | − | − | − | + |
| Methyl red test | − | − | − | − |
| Nitrate reduction | + | − | + | + |
| Phenylalanine deaminase | − | − | − | − |
| Urease | + | + | + | + |
| Voges-proskauer test | − | − | − | − |
| Growth on MacConkey agar | + | + | + | + |
| Growth on Eosin methylene blue agar | + | + | + | + |
| Growth on Endo agar | + | + | + | + |
| Growth on Hektoen enteric agar | Restricted | − | Restricted | Restricted |

N.B. − (Negative); + (positive); nd (not determined).

The invention claimed is:

1. An isolated bacterial culture of RAY 132, identified as *Stenotrophomonas maltophilia* (ATCC#PTA-4233).

2. A composition of matter comprising an isolated sulfur-oxidizing plant growth promoting rhizobacterium (PGPR) RAY 132, identified as *Stenotrophomonas maltophilia* (ATCC#PTA-4233) and an agriculturally compatible carrier.

3. The combination according to claim 2 wherein the carrier is a seed.

4. The combination according to claim 3 wherein the sulfur-oxidizing PGPR is coated onto the seed.

5. The combination according to claim 4 wherein the seed is coated with peat or clay.

6. The combination according to claim 2 wherein the carrier is a liquid.

7. The combination according to claim 6 wherein the carrier is an agriculturally compatible oil.

8. The combination according to claim 4 wherein the coating is a polymer.

9. The combination according to claim 2 wherein the carrier is a granular material.

10. The combination according to claim 9 wherein the granular material is peat or clay or perlite granules, or a mixture thereof.

11. The combination according to claim 2 including at least one other biocontrol PGPR.

12. The combination according to claim 2 including at least one other PGPR.

* * * * *